(12) United States Patent
Qiu et al.

(10) Patent No.: US 6,571,446 B2
(45) Date of Patent: Jun. 3, 2003

(54) METHOD FOR MANUFACTURING PIEZOELECTRIC LUMINOUS ELEMENT

(75) Inventors: Hong Qiu, Beijing (CN); Koji Sumi, Nagano (JP); Tsutomu Nishiwaki, Nagano (JP)

(73) Assignee: Seiko Epson Corporation (JP)

( * ) Notice: Subject to any disclaimer, the term of this patent is extended or adjusted under 35 U.S.C. 154(b) by 79 days.

(21) Appl. No.: 09/916,747

(22) Filed: Jul. 30, 2001

(65) Prior Publication Data

US 2001/0054857 A1 Dec. 27, 2001

Related U.S. Application Data

(62) Division of application No. 09/458,665, filed on Dec. 10, 1999, now Pat. No. 6,281,617.

(30) Foreign Application Priority Data

Dec. 10, 1998 (JP) ............................................. 10-351076

(51) Int. Cl.[7] .............................................. H04R 17/00
(52) U.S. Cl. ........................ 29/25.35; 29/847; 216/5; 216/24; 310/311; 427/64; 427/100
(58) Field of Search ................................. 29/25.35, 846, 29/847; 216/5, 24; 427/64, 532, 150; 310/311, 323.09, 331, 382

(56) References Cited

U.S. PATENT DOCUMENTS

| 4,532,454 A | * | 7/1985 | Abdalla ........................ 313/506 |
| 4,728,519 A | * | 3/1988 | Tanimoto ....................... 427/66 |
| 5,446,334 A | * | 8/1995 | Gaffney ........................ 310/338 |
| 5,905,260 A | * | 5/1999 | Sage et al. .................... 250/306 |
| 6,117,574 A | * | 9/2000 | Watanabe et al. ............. 428/698 |
| 6,207,077 B1 | * | 3/2001 | Burnell-Jones ............. 252/301.36 |

OTHER PUBLICATIONS

Kitamura et al., "Triboluminescence In N–Alkyl and N–Alkyl–3–Substituted Carbazole Crystals", Chemical Physics Letters, vol. 125, No. 4, Apr. 11, 1986.
Chapman et al., "Triboluminescence of glasses and quartz", J. Appl. Phys. 54 (10), Oct. 1983, ©1983 American Institute of Physics.
Jeffrey I. Zink, "Triboluminescence", Accounts of Chemical Research, vol. II, No. 8, Aug. 1978, © 1978 American Chemical Society.
Takada et al., "Transicent Behavior of Mechanoluminescence from Europium Complex in Powder and in Polymer–Dispersed Film", UPS–8, 1997.
Smiel et al., "Broadband triboluminescence in silica core fiber optic waveguides", Appl. Phys. Lett. 41(4), Aug. 15, 1982, ©1982 American Institute of Physics.

* cited by examiner

Primary Examiner—Peter Vo
Assistant Examiner—Donghai Nguyen
(74) Attorney, Agent, or Firm—Sterne, Kessler, Goldstein & Fox P.L.L.C.

(57) ABSTRACT

A method for manufacturing a piezoelectric element is disclosed. The method includes the steps of forming a lower electrode over a substrate, forming a piezoelectric luminous film over the lower electrode, forming an upper electrode over the piezoelectric film, forming a pressure luminous layer for emitting light upon application of pressure on the upper electrode, and attaching a substrate to the pressure luminous layer—has been inserted as a new abstract.

7 Claims, 2 Drawing Sheets

FIG. 1
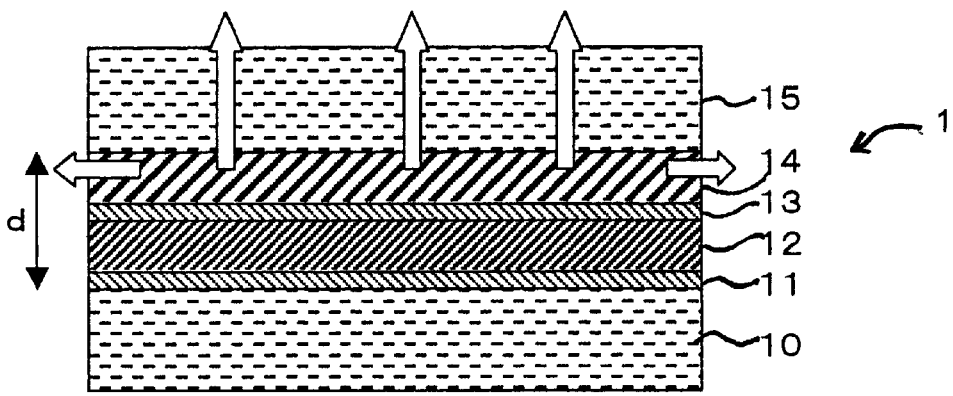
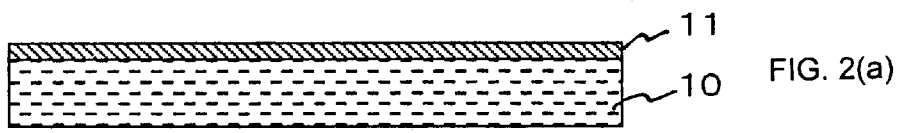
FIG. 2(a)
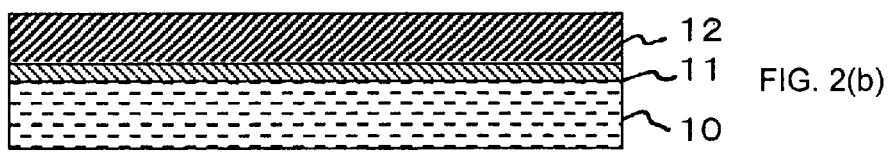
FIG. 2(b)
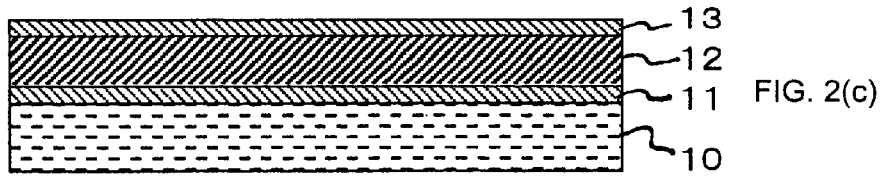
FIG. 2(c)
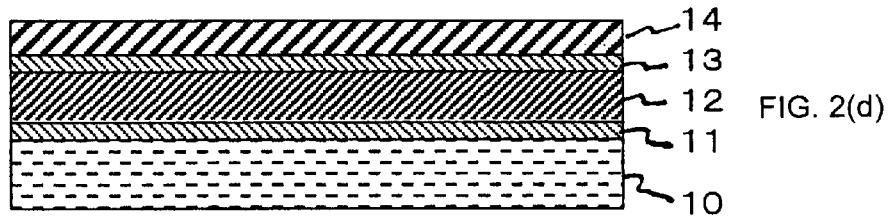
FIG. 2(d)
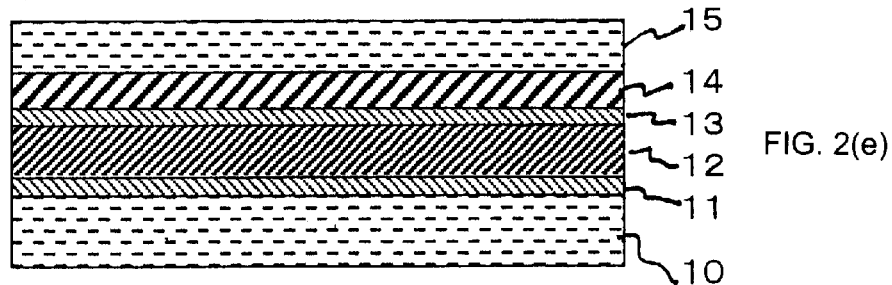
FIG. 2(e)

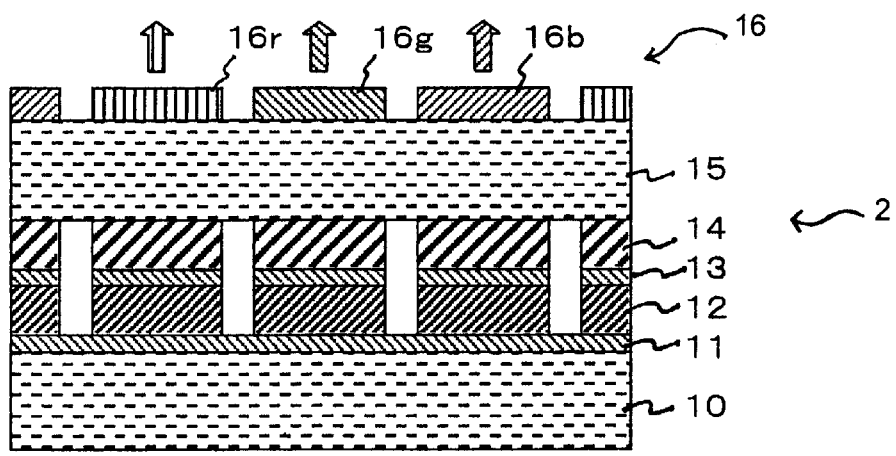
FIG. 3 Color Filter/Fluorescence Conversion Layer
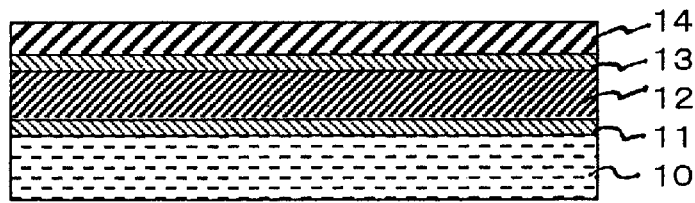
FIG. 4(a)
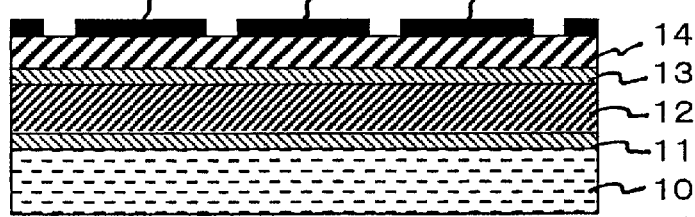
FIG. 4(b)
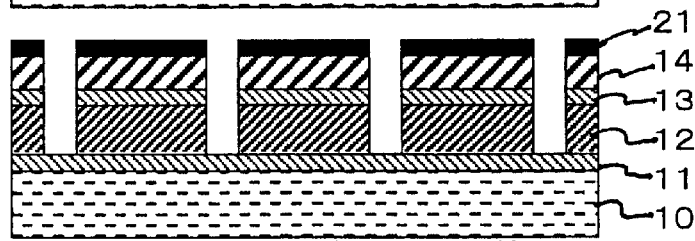
FIG. 4(c)
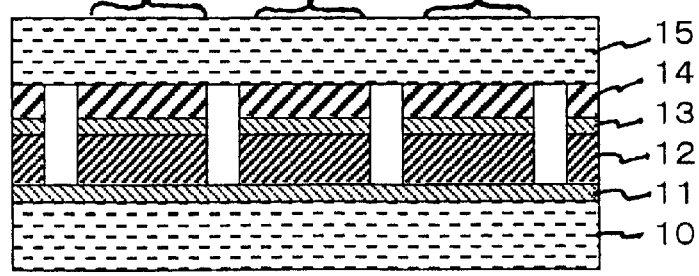
FIG. 4(d)

METHOD FOR MANUFACTURING PIEZOELECTRIC LUMINOUS ELEMENT

This is a divisional of application Ser. No. 09/458,665 filed on Dec. 10, 1999 and now U.S. Pat. No. 6,281,617.

BACKGROUND OF THE INVENTION

1. Field of the Invention

The present invention relates to a luminous element which can be used for, for example, a display device. More particularly, this invention relates to a proposal of a new luminous element which uses a material capable of emitting light upon sensing pressure.

2. Description of Related Art

As various energies are applied to a substance, electrons in the substance transit from the ground state to the excited state and then return to the ground state, and the substance sometimes emits light. This is generally called a luminescence phenomenon. It has been confirmed that specific substances exhibit a tribo-luminescence phenomenon in which they emit light upon the application of friction or pressure.

For example, a treatise of R. Nowak et al. entitled "Efficient Triboluminescence in N-isopropylcarbazole" (Chemical Physics Letters, Vol. 94, No. 3, Jan. 21, 1983) describes that when pressure is applied to crystals of N-isopropylcarbazole, the crystals emit blue light of wavelengths of 400 nm to 500 nm. Moreover, a treatise of A. J. Smiel entitled "Triboluminescence of Silica Core Optical Fibers" (Appl. Phys. Lett. 40(2), Jan. 15, 1982) and a treatise entitled "Broadband Triboluminescence in Silica Core Fiber Optic Waveguides" (Appl. Phys. Lett. 41(4), Aug. 15, 1982) describe that amorphous glass of $SiO_2$ emits blue, red, or white light. Also, a treatise of Takada et al. entitled "Transient Behavior of Mechanoluminescence from Europium Complex in Powder and in Polymer-Dispersed Film" (UPS-8, 1997) describes that a substance called $Eu(TTA)_3$ emits red light. Furthermore, a treatise of J. I. Zink entitled "Accounts of Chemical Research" (Vol. 11, No. 8, August 1978, p.p. 289–295) and a treatise of Linda M. Sweeting et al. entitled "Crystal Structure and Triboluminescence 2. 9-Anthracenecarboxylic Acid and Its Esters" (Chem. Mater. Vol. 9, No. 5, 1997, p.p. 1103–1115) describe a substance that exhibits a tribo-luminescence phenomenon.

Although research has been conducted on this tribo-luminescence phenomenon, the commercialization of such a phenomenon has not been realized.

SUMMARY OF THE INVENTION

By making use of the inventor's experiences in a piezoelectric element, the commercialization of which has been promoted through years of studies, the inventor of this application has devised a specific structure to realize a luminous element and a display device, which utilize this tribo-luminescence phenomenon, and a method for manufacturing the luminous element and the display device.

It is an object of this invention to provide a piezoelectric luminous element which utilizes a tribo-luminescence phenomenon.

It is another object of this invention to provide a display device which utilizes the tribo-luminescence phenomenon.

It is still another object of this invention to provide a specific method for manufacturing a piezoelectric luminous element which utilizes the tribo-luminescence phenomenon.

It is a further object of this invention to provide a specific method for manufacturing a display device which utilizes the tribo-luminescence phenomenon.

This invention is a piezoelectric luminous element comprising:
a pressure luminous layer for emitting light upon the application of pressure; and
a piezoelectric element comprising a piezoelectric film held between electrode films and being located so as to be capable of applying pressure on the pressure luminous layer.

The pressure luminous layer is formed with any one luminescent material selected from a group consisting of N-isopropylcarbazole, silicon oxide glass, and $Eu(TTA)_3$.

Moreover, the invention may be structured in a manner such that the pressure luminous layer and the piezoelectric element may be held between substrates such that the distance between these substrates will not change. It is desirable that of the substrates, the substrate placed in contact with the side of the pressure luminous layer where the piezoelectric element is not provided be capable of transmitting light.

This invention is a display device comprising the piezoelectric luminous element of the present invention, wherein the display device has a piezoelectric luminous unit, which is composed of at least the piezoelectric film, one of the electrodes, and the pressure luminous layer, and which is held between the substrates in a manner such that it can be activated independently in accordance with a picture element area.

Moreover, this display device may comprise a fluorescence conversion layer for converting the wavelength of the pressure luminous layer in accordance with the piezoelectric luminous unit on the substrate placed in contact with the light-emitting side of the pressure luminous layer.

Furthermore, the display device may comprise a color filter for transmitting a specific wavelength in accordance with the piezoelectric luminous unit on the substrate placed in contact with the light-emitting side of the pressure luminous layer.

This invention is a method for manufacturing a piezoelectric luminous element, comprising the steps of:
forming a lower electrode over a substrate;
forming a piezoelectric film over the lower electrode;
forming an upper electrode over the piezoelectric film;
forming a pressure luminous layer for emitting light upon the application of pressure on the upper electrode; and
attaching a substrate to the pressure luminous layer.

For example, the step of forming the pressure luminous layer comprises the steps of:
applying a mixture of a resin and N-isopropylcarbazole powder to the upper electrode; and
drying the applied mixed resin at a constant temperature.

Also, for example, the step of forming the pressure luminous layer comprises the steps of:
forming an amorphous silicon film over the upper electrode; and
forming a silicon oxide glass film by giving thermal treatment to the silicon film in an oxygen atmosphere.

Moreover, the step of forming the pressure luminous layer comprises the steps of:
generating a methylene chloride solution by mixing polycarbonate and a europium compound;
applying the solution to the upper electrode; and
drying the applied solution.

Furthermore, the step of forming the piezoelectric film comprises the steps of:

applying, drying and pyrolyzing a piezoelectric ceramic precursor; and crystallizing the piezoelectric ceramic precursor.

In the step of crystallizing the piezoelectric ceramic precursor, crystallization is caused by laser irradiation, dipping in an alkali solution of fixed concentration, or high temperature thermal treatment.

This invention is a method for manufacturing a display device, comprising the steps of:

forming a lower electrode over a substrate;

forming a piezoelectric film over the lower electrode;

forming an upper electrode over the piezoelectric film;

forming a pressure luminous layer for emitting light upon the application of pressure on the upper electrode;

etching the piezoelectric film, the upper electrode, and the pressure luminous layer in a pattern corresponding to a picture element area; and attaching a substrate to the etched pressure luminous layer.

BRIEF DESCRIPTION OF THE DRAWINGS

FIG. 1 is a sectional view of the layer structure of a piezoelectric luminous element according to Embodiment 1.

FIGS. 2a to 2e show sectional views illustrative of the steps of manufacturing the piezoelectric luminous element according to Embodiment 1.

FIG. 3 is a sectional view of the layer structure of a piezoelectric luminous element according to Embodiment 2.

FIGS. 4a to 4d show sectional views illustrative of the steps of manufacturing the piezoelectric luminous element according to Embodiment 2.

DESCRIPTION OF THE PREFERRED EMBODIMENTS

Preferred embodiments of this invention are hereinafter explained with reference to the attached drawings.
(Embodiment 1)

Embodiment 1 of this invention relates to a basic structure of a luminous element which utilizes a tribo-luminescence phenomenon, and to a method for manufacturing such a luminous element. FIG. 1 is a sectional view of a piezoelectric luminous element of this invention. White arrows in the drawing indicate the directions in which light is emitted.

As shown in FIG. 1, a piezoelectric luminous element 1 of this invention comprises a substrate 10, an electrode film 11, a piezoelectric film 12, an electrode film 13, a pressure luminous layer 14, and a transparent substrate 15.

The substrates 10 and 15 are composed of materials which have a certain degree of mechanical strength, such as silicon, various kinds of inorganic oxides (glass, quartz, magnesium oxide, zinc oxide), and resin. However, the substrate 15 placed on the side where light from the pressure luminous layer 14 should be transmitted has to be capable of transmitting light. The thickness of the substrates can be adjusted as appropriate in accordance with the specification of a relevant product.

The electrode films 11 and 13 are the electrodes to apply voltage to the piezoelectric film 12. They are formed with conductive materials such as platinum (Pt), iridium (Ir), ITO ($In_2O_3$+5% $SnO_2$), $SnO_2$, $In_2O_3$, or ZnO. Each electrode film is formed with a thickness of, for example, about 200 nm.

The piezoelectric film 12 is composed of crystals of normal piezoelectric ceramic. Examples of preferred materials are ferroelectric piezoelectric materials such as lead zirconate titanate (PZT), and such other materials obtained by adding metallic oxide such as niobium oxide, nickel oxide or magnesium oxide to the above-mentioned ferroelectric ceramic materials. The composition of the piezoelectric film 12 is selected as appropriate in consideration of the properties, usage, and other factors of the piezoelectric element. Specifically, lead titanate ($PbTiO_3$), lead zirconate titanate ($Pb(Zr,Ti)O_3$), lead zirconate ($PbZrO_3$), lead lanthanum titanate (($Pb,La)TiO_3$), lead lanthanum zirconate titanate (($Pb,La$) ($Zr,Ti)O_3$), or lead magnesium neobate zirconate titanate ($Pb$ ($Zr,Ti$) ($Mg,Nb)O_3$) can be used. The thickness of the piezoelectric film is adjusted to the degree that allows the pressure luminous layer to emit sufficient light by means of displacements caused by the application of an electric field.

The pressure luminous layer 14 is composed of materials that exhibit the tribo-luminescence phenomenon where the application of pressure causes the emission of light. For example, if N-isopropylcarbazole is used, it is possible to generate strong blue light (with a wavelength of 400 nm to 500 nm). If silicon oxide ($SiO_x$: $0>x\leq2$) glass is used, it is possible to generate blue light (with a wavelength of 430 nm), red light (with a wavelength of 630 nm), or white light (with a wavelength of 380 nm to 900 nm) in accordance with changes in the state of bonding between Si atoms and O atoms according to conditions at the time of the film formation. If $Eu(TTA)_3$ is used, it is possible to generate red light (with a wavelength of 610 nm). If phenanthrene is used, blue light with a wavelength of 400 nm to 440 nm can be obtained. If coumarin is used, light with wavelengths of 390 nm to 450 nm can be obtained. If m-aminophenol is used, ultraviolet rays with wavelengths of about 340 nm can be emitted, and it is thereby possible to use this invention for the irradiation of light other than visible light. If phthalic anhydride is used, light with wavelengths of 360 nm to 420 nm can be obtained. If $(CH_3P)_2C$ is used, light with wavelengths of 480 nm to 500 nm can be obtained. It is confirmed that other materials such a dibromobis (triphenylphosphine) manganese, uranyl oxalate hexahydrate, and 9-anthracenecarboxylic acid and its ester also exhibit the tribo-luminescence phenomenon and, therefore, can be used as the pressure luminous layer.
(Action)

In the above-described structure, the application of a given voltage between the electrodes 11 and 13 generates an electric field between the electrodes, thereby causing the crytals of the piezoelectric film 12 to exhibit an electromechanical transducing action and to deform. Stress caused by this deformation act in the surface direction of the piezoelelectric film. However, since the distance between the substrates 10 and 15 is set as a distance d and does not change, the displacement of the piezoelectric film directly deforms the pressure luminous layer 14. Deformation causes a strong electric field on the surface portion of the pressure luminous layer 14. This electric field activates $N_2$ existing in the vicinity of the surface, and light is emitted there. Moreover, this light activates the luminous layer material and other portions of the pressure luminous layer 14 also emit light. Furthermore, the application of pressure on the pressure luminous layer excites electrons in the pressure layer, and the pressure luminous layer thereby emits light when the energy level of electron returns to the ground state. This light is transmitted through the transparent substrate 15 and is then emitted externally. In the above-mentioned documents, it is stated that impurities and defects existing in tribo-luminescence materials, or rare earth elements added to the tribo-luminescence materials determine the light-emitting properties. Consequently, it is possible to adjust the color of the emitted light by adjusting such conditions.
(Manufacturing Method)

A method for manufacturing a piezoelectric element of this invention is hereinafter explained with reference to FIGS. 2a to 2e, sectional views illustrative of the manufacturing steps.

Piezoelectric Element Forming Step (FIGS. 2(a) through (c))

The piezoelectric element forming step is the step of forming, over the surface of a substrate 10, a piezoelectric element which is composed of a piezoelectric film 12 held between electrode films 11 and 13.

First, the electrode film 11 is formed over the substrate 10 (FIG. 2(a)). Example materials of the electrode film are platinum (Pt), iridium (Ir), ITO ($In_2O_3+5\%$ $SnO_2$), $SnO_2$, $In_2O_3$, and ZnO. As for the method for forming the electrode film, a normal method for forming a conductive metal film is applied. For example, if Pt is used as the electrode film, a sputtering method is employed. If ITO is used as the electrode film, the sputtering method or an electron beam vapor deposition method is employed. As for the thickness of the electrode film 11, some hundreds of nanometers will suffice.

Next, the piezoelectric film 12 is formed (FIG. 2(b)). As for the method for forming the piezoelectric film, a normally employed method for crystallizing piezoelectric ceramics is applied. For example, a sol which is made of a starting materials for PZT, namely metal alkoxides, acetates and so on is applied by coating method such as a spin coating method. Subsequently, drying is performed at a temperature of about 180° C. for about 10 minutes and pyrolysis is then performed at a temperature of about 400° C. for about 30 minutes. Such drying and pyrolysis causes the metal alkoxide in the sol and the acetate to undergo thermal decomposition of ligands, therby forming a metal-oxygen-metal network. The above-described cycle is repeated for a certain number of times (for example, eight times) to laminate a multiplicity of piezoelectric thin films. After the piezoelectric thin films are laminated a certain number of times, crystallization is conducted to crystallize the laminated gel.

As for the crystallization, it is possible to adopt various methods such as a method of using a laser, a method of performing hydrothermal treatment, and a method of performing fast thermal treatment. In the case of the using a laser a KrF laser with a light emission wavelenght of 248 nm is used. This laser light is irradiated with 30 ns pulses and with the output of about 300–700 $mJ/cm^2$. In the case of hydrothermal treatment, the treatment is conducted at a temperature of about 130° C. for about 90 minutes in an alkali solution ($Ba(OH)_2$) in concentration of about 0.05 M. In the case of fast thermal treatment, burning if conducted at a temperature of about 650° C. for about 5 minutes and at a temperature of about 900° C. for about one minute. Through the above-described treatment, a peroviskite crystal structure having any of the relevant crystal structrues is formed out of the gel in the amorphous state.

Subsequently, the electrode film 13 is formed (FIG. 2(c)). This electrode film is formed in the same manner as the electrode film 11.

Pressure Luminous Layer Forming Step (FIG. 2(d))

The pressure luminous layer forming step is the step of forming, over the piezoelectric element, the pressure luminous layer with a material that exhibits the tribo-luminescence phenomenon. An appropriate manufacturing method differs depending on the luminescent material to be used.

For example, if N-isopropylcarbazole is used as the luminescent material, N-isopropylcarbazole powder is first mixed into a binder resin. The resin with this powder mixed therein is then applied to the electrode film 13 of the piezoelectric element. As for the coating method, it is possible to employ various kinds of coating methods which are normally used. For example, coating can be performed by printing. The applied resin is dried at a fixed temperature (for example, 100° C.) and is thereby hardened. If a thermosetting resin is used as this resin, it is possible to harden it by heating.

If $SiO_x$ ($0<x\leq 2$) is used, an amorphous silicon film is first formed over the electrode film 13. Thermal treatment is given to this silicon film at a fixed temperature (for example, in the range of 800° C. to 1200° C.) in an oxygen atmosphere, thereby producing a silicon oxide glass film. It is possible to change the color of the emitted light into any of red, blue, and white colors by adjusting the bonding state between Si and O by changing the temperature of the above-described thermal treatment.

If $Eu(TTA)_3$ is used, polycarbonate is first mixed with a europium compound, thereby generating a methylene chloride solution. For example, 90 wt % polycarbonate is mixed with 10 wt % europium. Then, this solution is applied to the electrode film 13. The applied solution is dried under certain conditions.

Substrate Attaching Step (FIG. 2(e))

After the pressure luminous layer is formed, the substrate 15 is attached to the pressure luminous layer as a last step. After the attachment of the substrate, some measure should be taken so that the distance d between the substrates 10 and 15 will not change freely, for example, by placing the laminated body obtained above in a housing that can keep and fix the distance d almost constant, or by molding the peripheries of the laminated body obtained above with a resin. It is certainly necessary to carry out wiring in order to apply an electric field to the piezoelectric element.

As described above, according to Embodiment 1, the piezoelectric element applies pressure on the luminescent material, which exhibits the tribo-luminescence phenomenon, thereby generating pressure. Accordingly, it is possible to provide a luminous element which emits light without generating heat. Therefore, it is possible to provide a luminous element which does not generate heat.

According to Embodiment 1, by using N-isopropylcarbazole as the luminescent material, it is possible to cause the emission of strong blue light.

According to Embodiment 1, by using $SiO_x$ ($0<x\leq 2$) glass as the luminescent material and by adjusting the manufacturing conditions, it is possible to cause the emission of light of various colors.

According to Embodiment 1, by using $Eu(TTA)_3$, it is possible to cause the emission of red light.

(Embodiment 2)

Embodiment 2 of this invention relates to a display device composed of a luminous element which utilizes the tribo-luminescence phenomenon, and also to a method for manufacturing such a display device.
(Structure)

FIG. 3 is a sectional view of the display device of Embodiment 2. Arrows in the drawing indicate the direction in which light is emitted.

As shown in FIG. 3, a display device 2 of this invention comprises a substrate 10, an electrode film 11, a piezoelectric film 12, an electrode film 13, a pressure luminous layer 14, a transparent substrate 15, and a color filter or fluorescence conversion layer 16. The substrate 10, the electrode film 11, the piezoelectric film 12, the electrode film 13, the pressure luminous layer 14, and the transparent substrate 15 can be considered as similar to those of Embodiment 1. However, in this embodiment, it is necessary to cause the emission of light independently for each picture element. Therefore, a multiplicity of electric field luminous units 1r, 1g, or 1b are provided, which are patterned in accordance with picture element areas composed of the piezoelectric film 12, the electrode film 13, and the pressure luminous layer 14. There is an appropriate gap between adjacent electric field luminous units.

The color filter or fluorescence conversion layer 16 is a component which is required when it is desirable to adjust the wavelengths of light from the pressure luminous layer 14. For example, a color display device needs three primary colors of red, green, and blue.

If silicon oxide glass which causes the emission of white light is used as the pressure luminous layer, such a color filter 16 is provided for transmitting the respective wavelengths corresponding to the primary colors contained in the white color. A red filter 16r is provided for a picture element corresponding to a red color, a green filter 16g is provided for a picture element corresponding to a green color, and a blue filter 16b is provided for a picture element corresponding to a blue color.

If N-isopropylcarbazole is used as the pressure luminous layer, the color of the emitted light is blue and, therefore, it is necessary to change the color of the emitted light at the picture element corresponding to the red color and at the picture element corresponding to the green color. In this case, at the picture element corresponding to the red color, the fluorescence conversion layer 16 is used which is composed of a wavelength converting substance capable of absorbing the blue light and converting it into a red light, thereby causing the emission of the red light. For example, perylene can be used as the wavelength converting substance for the red color. At the picture element corresponding to the green color, the fluorescence conversion layer 16 is used which is composed of a wavelength converting substance capable of absorbing the blue light and converting it into a green light, thereby causing the emission of the green light. For example, coumarin 6 can be used as the wavelength converting substance for the green color. At the picture element corresponding to the blue color, no fluorescence conversion layer is provided and the light from the pressure luminous layer is made to emit as it is. Other example materials of the fluorescence conversion layer are DCM1, quinacridone, rubrene, DCJT, and Nile red.

Since the electrode film 11 is made to function as a common electrode, it is connected to an earth electrode of a drive circuit (not shown in the drawing). The electrode films 13 of the respective electric field luminous units are individually connected to drive terminals of the drive circuit. This structure relates to an active matrix system for activating the respective picture elements by means of active elements. If the display device is to be composed in a simple matrix system, it is necessary to pattern both the electrode films 11 and 13 independently in stripes and to carry out wiring in an X–Y matrix structure.

In the above-described structure, when the drive circuit (not shown) applies voltage between the electrode film 11, which is a common electrode, and any of the electrode films 13, any of the piezoelectric elements in the electric field luminous units (picture element areas) 1r, 1g, or 1b deforms. This deformation acts on the pressure luminous layer 14 in the relevant electric field luminous units, thereby exhibiting the tribo-luminescence phenomenon and causing the emission of light. If voltage is applied to the electric field luminous unit 1r corresponding to the red picture element, red light is emitted. If voltage is applied to the electric field luminous unit 1g corresponding to the green picture element, green light is emitted. If voltage is applied to the electric field luminous unit 1b corresponding to the blue picture element, blue light is emitted. With the color picture elements composed of such luminous layers, it is possible to cause the emission of light in any color by synthesizing colors depending on the existence or nonexistence of, or the strength of, the emitted light of the respective primary colors.

(Manufacturing Method)

A method for manufacturing the display device of Embodiment 2 is hereinafter explained with reference to FIGS. 4a and 4d, sectional views illustrative of the manufacturing steps.

The step of forming the pressure luminous layer 14 (FIG. 4(a)) is similar to that of Embodiment 1 (FIGS. 2(a) through 2(d)). The subsequent step prior to the attachment of the substrate 15 is the step of conducting patterning for each picture element and dividing the relevant films into electric field luminous units.

A photoresist 21 is first applied over the pressure luminous layer 14, and exposure and development are conducted in accordance with the pattern of the picture element areas, thereby leaving the photoresist 21 only in the picture element areas (FIG. 4(b) In this step, a normal photolithography method can be employed. It is possible to arbitrarily select gaps between the picture element areas. However, if the gaps are too small and if the adjacent electric field luminous units are too close, the deformation at the time of activation may also cause the emission of light from the adjacent picture element areas. On the other hand, if the gaps are too large, the light emitting surface of the display device reduces and, therefore, the efficiency decreases. Appropriate gaps should be determined by keeping the above conditions in balance.

Etching is then conducted to remove the pressure luminous layer 14, the electrode film 13, and the piezoelectric film 12 (FIG. 4(c)). As for the etching method, either dry etching or wet etching may be employed. However, dry etching is preferred because it is possible to adjust the depth of etching delicately. It is necessary to control the depth of etching delicately so that the electrode film 11 can be left without being etched as the common electrode.

After the etching is finished, the transparent substrate 15 is attached to the pressure luminous layer in the same manner as in FIG. 2(e). In order to manufacture a color display device, the color filter or the fluorescence conversion layer 16 is formed in accordance with the colors set in the picture element areas. Whether the color filter or the fluorescence conversion layer should be adopted is determined in accordance with the color of the light emitted from the pressure luminous layer as stated above. In the case of the color filter, pigments are mixed in a transparent resin or dyes are used, and patterning is then performed. In the case of the fluorescence conversion layer, a fluorescence converting material is applied to the pressure luminous layer, and patterning is then performed. Partitions may be formed between the picture element areas, and the materials for the color filter or the fluorescence converting materials may be selected to fill the respective picture element areas and may be dried.

Embodiment 2 can give the same advantageous effects as those of Embodiment 1. Moreover, as it is composed to enable the emission of primary color light for each picture element, it is possible to provide a display device capable of realizing color display.

(Other Variations)

The present invention is not limited to the respective embodiments described above and can be applied in many variations. For example, materials for the pressure luminous layer are not limited to those mentioned in the above embodiments, but any materials that exhibit the tribo-luminescence phenomenon can be used.

Moreover, the layer structures of the piezoelectric luminous element and the display device are not limited to those described above, and it is possible to change the number of laminated layers and the arrangement of the layers in various ways. For example, if only one piezoelectric element cannot produce enough stress, it is possible to provide two or more piezoelectric elements and to make the stress from these piezoelectric elements simultaneously apply to the pressure luminous layer. As an example of such a structure, the pressure luminous layer maybe held between two piezoelectric elements.

This invention makes it possible to provide a new luminous element and a new display device which utilize the tribo-luminescence phenomenon and which have not been commercialized. Since the luminous element and the display device is not treated at high temperatures, it is possible to provide a light source with a small temperature increase and of high reliability.

As the intensity of the emitted light is detected, it is possible to use this invention for the indirect measurement of displacement of the piezoelectric element.

What is claimed is:

1. A method for manufacturing a piezoelectric luminous element, comprising the steps of:
    forming a lower electrode over a substrate;
    forming a piezoelectric film over the lower electrode;
    forming an upper electrode over the piezoelectric film;
    forming a pressure luminous layer for emitting light upon application of pressure on the upper electrode; and
    attaching a substrate to the pressure luminous layer.

2. A method for manufacturing a piezoelectric luminous element according to claim 1, wherein the step of forming the pressure luminous layer comprises the steps of:
    applying a mixture of a resin and N-isopropylcarbazole powder to the upper electrode; and
    drying the applied mixed resin at a constant temperature.

3. A method for manufacturing a piezoelectric luminous element according to claim 1, wherein the step of forming the pressure luminous layer comprises the steps of:
    forming an amorphous silicon film over the upper electrode; and
    forming a silicon oxide glass film by giving thermal treatment to the silicon film in an oxygen atmosphere.

4. A method for manufacturing a piezoelectric luminous element according to claim 1, wherein the step of forming the pressure luminous layer comprises the steps of:
    generating a methylene chloride solution by mixing polycarbonate and a europium compound;
    applying the solution to the upper electrode; and
    drying the applied solution.

5. A method for manufacturing a piezoelectric luminous element according to claim 1, wherein the step of forming the piezoelectric film comprises the steps of:
    applying, drying and pyrolyzing a piezoelectric ceramic precursor; and
    crystallizing the piezoelectric ceramic precursor.

6. A method for manufacturing a piezoelectric luminous element according to claim 5, wherein in the step of crystallizing the piezoelectric ceramic precursor, crystallization is caused by laser irradiation, hydrothermal treatment in an alkali solution of fixed concentration, or high temperature thermal treatment.

7. A method of manufacturing a display device comprising the steps of:
    forming a lower electrode over a substrate;
    forming a piezoelectric film over the lower electrode;
    forming an upper electrode over the piezoelectric film;
    forming a pressure luminous layer for emitting light upon application of pressure on the upper electrode;
    etching the piezoelectric film, the upper electrode, and the pressure luminous layer in a pattern corresponding to a picture element area; and
    attaching a transparent substrate to the etched pressure luminous layer; and
    forming a color filter or a fluorescence conversion layer on the transparent substrate in accordance with the pressure luminous element area.

* * * * *